US009968372B2

(12) United States Patent
Chen et al.

(10) Patent No.: US 9,968,372 B2
(45) Date of Patent: May 15, 2018

(54) CANNULA INSERTION TOOL

(71) Applicant: Medical Instrument Development Laboratories, Inc., San Leandro, CA (US)

(72) Inventors: David Chen, Fremont, CA (US); Steven Smith, Alameda, CA (US)

(73) Assignee: Medical Instrument Development Laboratories, Inc., San Leandro, CA (US)

( * ) Notice: Subject to any disclaimer, the term of this patent is extended or adjusted under 35 U.S.C. 154(b) by 511 days.

(21) Appl. No.: 14/044,651

(22) Filed: Oct. 2, 2013

(65) Prior Publication Data

US 2015/0094751 A1    Apr. 2, 2015

(51) Int. Cl.
| A61B 17/34 | (2006.01) |
| A61F 9/007 | (2006.01) |
| A61M 5/158 | (2006.01) |

(52) U.S. Cl.
CPC .......... *A61B 17/34* (2013.01); *A61B 17/3421* (2013.01); *A61B 17/3496* (2013.01);
(Continued)

(58) Field of Classification Search
CPC . A61B 17/34; A61B 17/3496; A61B 17/3417; A61B 2017/34;
(Continued)

(56) References Cited

U.S. PATENT DOCUMENTS

| 1,434,388 A | 11/1922 | Hughes |
| 3,190,661 A | 6/1965 | Wahl et al. |

(Continued)

FOREIGN PATENT DOCUMENTS

| CN | 302968131 | 10/2014 |
| CN | 303114901 | 2/2015 |

(Continued)

OTHER PUBLICATIONS

Pallucci, Description d'un nouvel instrument propre a abraiser la cataracte avec tout le success possible. Paris: Son of d'Houry, 1 page, 1750.

(Continued)

*Primary Examiner* — Christopher L Templeton
*Assistant Examiner* — Majid Jamialahmadi
(74) *Attorney, Agent, or Firm* — Michael Best & Friedrich LLP

(57) ABSTRACT

A cannula insertion tool includes a body having a first end portion, a second end portion, and a grip located between the first end portion and the second end portion. The body defines a channel extending through the first end portion and the grip. The insertion tool also includes a slider having a drive member and an actuator. The drive member is positioned within the channel of the body. The actuator extends outwardly from the second end portion of the body. The insertion tool further includes a needle coupled to the drive member adjacent the first end portion of the body. The needle is movable with the slider between a retracted position, in which the needle is positioned substantially within the first end portion of the body, and an extended position, in which at least a portion of the needle extends outwardly from the first end portion of the body.

24 Claims, 7 Drawing Sheets

(52) U.S. Cl.
CPC .......... *A61F 9/007* (2013.01); *A61B 17/3468* (2013.01); *A61M 2005/1585* (2013.01)

(58) Field of Classification Search
CPC ...... A61B 2017/3405; A61B 2019/545; A61B 17/3421; A61B 17/3494; A61B 2017/2918; A61B 2017/32113; A61B 2090/3937; A61B 2090/395; A61B 17/3415; A61B 17/3468; A61F 9/007; A61M 2005/1585; A61M 2005/3252; A61M 2005/3228; A61M 2005/3227; A61M 25/0631; B41K 1/02; B41K 1/04; B41K 1/08; B41K 1/34; B41K 1/15; B43K 24/02; B43K 24/026; B43K 24/04; B43K 24/08
USPC ....... 606/185, 167, 181, 107, 184, 186, 187, 606/188, 189; 604/6.05, 181, 136, 137, 604/164.12, 264, 164.08; 401/35; 101/372; 30/162, 335

See application file for complete search history.

(56) References Cited

U.S. PATENT DOCUMENTS

| | | | |
|---|---|---|---|
| 3,313,299 A | 4/1967 | Spademan | |
| 3,510,177 A | 5/1970 | Shimula | |
| 3,568,436 A | 3/1971 | Heffner et al. | |
| 3,776,238 A | 12/1973 | Peyman et al. | |
| 3,815,604 A | 6/1974 | O'Malley et al. | |
| 3,829,104 A | 8/1974 | Green | |
| 3,853,127 A | 12/1974 | Spademan | |
| 3,884,238 A | 5/1975 | O'Malley et al. | |
| 4,011,869 A | 3/1977 | Seiler, Jr. | |
| 4,146,237 A | 3/1979 | Bergman | |
| 4,177,814 A | 12/1979 | Knepshield et al. | |
| 4,222,575 A | 9/1980 | Sekiguchi et al. | |
| 4,413,829 A | 11/1983 | Pietsch | |
| 4,530,359 A | 7/1985 | Helfgott et al. | |
| 4,590,935 A | 5/1986 | Ranalli | |
| 4,653,513 A | 3/1987 | Dombrowski | |
| 4,655,743 A | 4/1987 | Hyde | |
| 4,655,752 A | 4/1987 | Honkanen et al. | |
| 4,693,343 A | 9/1987 | Boyd | |
| 4,696,298 A | 9/1987 | Higgins et al. | |
| 4,756,536 A | 7/1988 | Belcher | |
| 4,759,359 A | 7/1988 | Willis et al. | |
| 4,819,635 A | 4/1989 | Shapiro | |
| 4,895,147 A | 1/1990 | Bodicky et al. | |
| 4,958,625 A | 9/1990 | Bates et al. | |
| 5,006,123 A * | 4/1991 | Soll ...................... | A61F 9/0136 33/512 |
| 5,009,435 A | 4/1991 | Villanyi et al. | |
| 5,019,035 A | 5/1991 | Missirlian et al. | |
| 5,041,095 A | 8/1991 | Littrell | |
| 5,176,628 A | 1/1993 | Charles et al. | |
| 5,284,472 A | 2/1994 | Sussman et al. | |
| 5,547,473 A | 8/1996 | Peyman | |
| 5,749,886 A * | 5/1998 | Abidin ............... | A61B 17/3211 30/162 |
| 5,752,938 A | 5/1998 | Flatland et al. | |
| 5,803,919 A | 9/1998 | Hart et al. | |
| 5,843,111 A | 12/1998 | Vijfvinkel | |
| 5,879,357 A | 3/1999 | Heaton et al. | |
| 5,979,494 A | 11/1999 | Perkins et al. | |
| 6,006,433 A | 12/1999 | Baltazar | |
| 6,139,560 A | 10/2000 | Kremer | |
| 6,277,102 B1 * | 8/2001 | Carilli ................. | A61M 5/1782 604/240 |
| D457,955 S | 5/2002 | Bilitz | |
| D460,279 S | 7/2002 | Moburg | |
| 6,439,541 B1 | 8/2002 | Nösel et al. | |
| 6,561,519 B1 | 5/2003 | Frese et al. | |
| 6,575,990 B1 | 6/2003 | Wang et al. | |
| 6,602,268 B2 | 8/2003 | Kuhr et al. | |
| D581,461 S | 11/2008 | Li | |
| 7,604,647 B2 | 10/2009 | Chen | |
| D612,052 S | 3/2010 | McCollam et al. | |
| D653,337 S | 1/2012 | Kampa et al. | |
| 8,591,463 B1 | 11/2013 | Cowe | |
| 8,845,584 B2 | 9/2014 | Ferguson et al. | |
| D732,661 S | 6/2015 | Dubuc et al. | |
| D733,289 S | 6/2015 | Blanchard et al. | |
| D733,869 S | 7/2015 | Ratjen | |
| D736,923 S | 8/2015 | Snow | |
| D741,992 S | 10/2015 | Roeper | |
| D745,664 S | 12/2015 | Pocock | |
| D746,443 S | 12/2015 | Chen | |
| 2003/0199827 A1 | 10/2003 | Thorne | |
| 2004/0092982 A1 | 5/2004 | Sheffer | |
| 2006/0089607 A1 * | 4/2006 | Chen .................. | A61B 17/3421 604/264 |
| 2006/0229563 A1 * | 10/2006 | O'Reagan ......... | A61M 25/0631 604/164.08 |
| 2007/0156224 A1 | 7/2007 | Cioanta | |
| 2009/0204135 A1 * | 8/2009 | Cote .................. | A61B 17/3211 606/167 |
| 2009/0297251 A1 * | 12/2009 | Sokoloff ................. | B43K 1/12 401/261 |
| 2010/0145352 A1 * | 6/2010 | Chang ............... | A61B 17/00234 606/110 |
| 2011/0094109 A1 * | 4/2011 | Chiu ...................... | A47L 13/022 30/162 |
| 2011/0282285 A1 | 11/2011 | Blanchard et al. | |
| 2012/0221036 A1 * | 8/2012 | Ahmann ................ | A61B 19/54 606/186 |
| 2013/0102967 A1 | 4/2013 | Hanlon et al. | |
| 2013/0110125 A1 * | 5/2013 | Silvestrini ............ | A61F 9/0017 606/107 |
| 2013/0274870 A1 | 10/2013 | Lombardi | |
| 2014/0094774 A1 | 4/2014 | Blanchard | |
| 2014/0276968 A1 | 9/2014 | Miksza | |
| 2015/0094751 A1 | 4/2015 | Chen et al. | |
| 2016/0074211 A1 | 3/2016 | Ko | |

FOREIGN PATENT DOCUMENTS

| | | |
|---|---|---|
| WO | 01/68016 | 9/2001 |
| WO | 0168016 A2 | 9/2001 |
| WO | 2006061027 A2 | 6/2006 |

OTHER PUBLICATIONS

Machemer et al., Vitrectomy: A Pars Plana Approach, Transactions American Academy of Ophthalmology and Otolaryngology, vol. 75, pp. 813-820, 1971.

Douvas, Microsurgical Pars Plana Lensectomy, Transactions American Academy of Ophthalmology and Otolaryngology, vol. 81, pp. 371-381, 1976.

Machemer et al., The Three-Port Microannular System for Closed Vitrectomy, American Journal of Ophthalmology, vol. 100, pp. 590-592, 1985.

Zinn et al., A New Endoillumination Infusion Cannula for Pars Plana Vitrectomy, Ophthalmic Surgery, vol. 11, pp. 850-855, 1980.

Gaynon et al., Four-Port Bimanual Vitrectomy, Arch Ophthalmol., vol. 10, pp. 1088-1089, 1986.

Co-pending U.S. Appl. No. 29/468,744, filed Oct. 2, 2013.

Photographs of Alcon Cannula System with Sclear Marker, publicly available before Oct. 2, 2013, 1 page.

MicroVision Incorporated, One-Step Trocar System—23 Ga, Jan. 2012, 1 page.

Alcon, Edge Plus Blade Valved Entry System, publicly available before Oct. 2, 2013, 1 page.

D.O.R.C., One Step 25 Gauge Transconjunctival System, 2012, 1 page.

MID Labs, Single Step Cannula Insertion Systems, Feb. 2012, 2 pages.

(56) References Cited

OTHER PUBLICATIONS

Extended European Search Report from the European Patent Office for Application No. 14187409.9 dated Jan. 23, 2015 (9 pages).

* cited by examiner

CANNULA INSERTION TOOL

BACKGROUND

The present invention relates to surgical tools and, more particularly, to trocar-cannula insertion tools for use in surgery of the posterior segment of the eye.

A trocar-cannula, such as a cannula insertion tool, is a surgical instrument. It can be used to create an incision and, in the same motion, place a cannula into the incision. The trocar-cannula is often comprised of two principal parts: (1) a hollow tube or cannula and (2) a puncturing member referred to as an obturator or trocar. The cannula is inserted through the wall of the body cavity with the assistance of the trocar passed through the cannula.

A trocar-cannula may be used in cardiovascular surgery, laparoscopic surgery, arthroscopic surgery, and intraocular surgery. In intraocular surgery, for example, a trocar-cannula is often used to obtain access to the posterior-segment of the eye (the area behind the lens). Typically, a cannula is positioned on a needle of a trocar for insertion into the eye. The needle is used to penetrate the eye and insert the cannula. Upon insertion of the cannula, the trocar can be removed from the eye while the cannula remains inserted in the eye.

SUMMARY

In one embodiment, the invention provides a cannula insertion tool including a body having a first end portion, a second end portion, and a grip located between the first end portion and the second end portion. The body defines a channel extending through the first end portion and the grip. The cannula insertion tool also includes a slider having a drive member and an actuator. The drive member is positioned within the channel of the body. The actuator extends outwardly from the second end portion of the body. The cannula insertion tool further includes a needle coupled to the drive member adjacent the first end portion of the body. The needle is movable with the slider between a retracted position, in which the needle is positioned substantially within the first end portion of the body, and an extended position, in which at least a portion of the needle extends outwardly from the first end portion of the body.

In another embodiment, the invention provides a cannula insertion tool including a body having an end portion and a grip. The body defines a channel extending through the end portion and the grip. The cannula insertion tool also includes a slider having a drive member and an actuator. The drive member is positioned within the channel of the body. The actuator extends outwardly from the body. The cannula insertion tool further includes a needle coupled to the drive member adjacent the end portion of the body. The needle is movable with the slider between a retracted position, in which the needle is positioned substantially within the body, and an extended position, in which at least a portion of the needle extends outwardly from the end portion of the body. The cannula insertion tool also includes a scleral marker coupled to and extending from the end portion of the body.

In yet another embodiment, the invention provides a cannula insertion tool including a body having a first end portion, a second end portion, a grip located between the first end portion and the second end portion, and a longitudinal axis extending through the first end portion, the grip, and the second end portion. The body defines a channel extending through the first end portion and the grip. The cannula insertion tool also includes a slider having a drive member and an actuator. The drive member is positioned within the channel of the body and has a first end and a second end. The actuator is coupled to the second end of the drive member and extends outwardly from the second end portion of the body. The cannula insertion tool further includes a needle coupled to the first end of the drive member adjacent the first end portion of the body. The needle is movable with the slider along the longitudinal axis between a retracted position, in which the needle is positioned substantially within the first end portion of the body, and an extended position, in which at least a portion of the needle extends outwardly from the first end portion of the body. The cannula insertion tool also includes a scleral marker coupled to and extending from the first end portion of the body in a direction generally parallel to the longitudinal axis.

In still another embodiment, the invention provides a method of performing an ophthalmic procedure. The method includes grasping an insertion tool with a single human hand. The insertion tool includes a body, a scleral marker on one end of the body, an opening formed in the body adjacent the scleral marker, and a needle. The needle is movable relative to the body between a retracted position and, through the opening, to an extended position. The method also includes marking a surgical site with the scleral marker while the insertion tool is grasped in the single human hand, and moving the needle to the extended position while the insertion tool is grasped in the single human hand.

Other aspects of the invention will become apparent by consideration of the detailed description and accompanying drawings.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Figure 1:
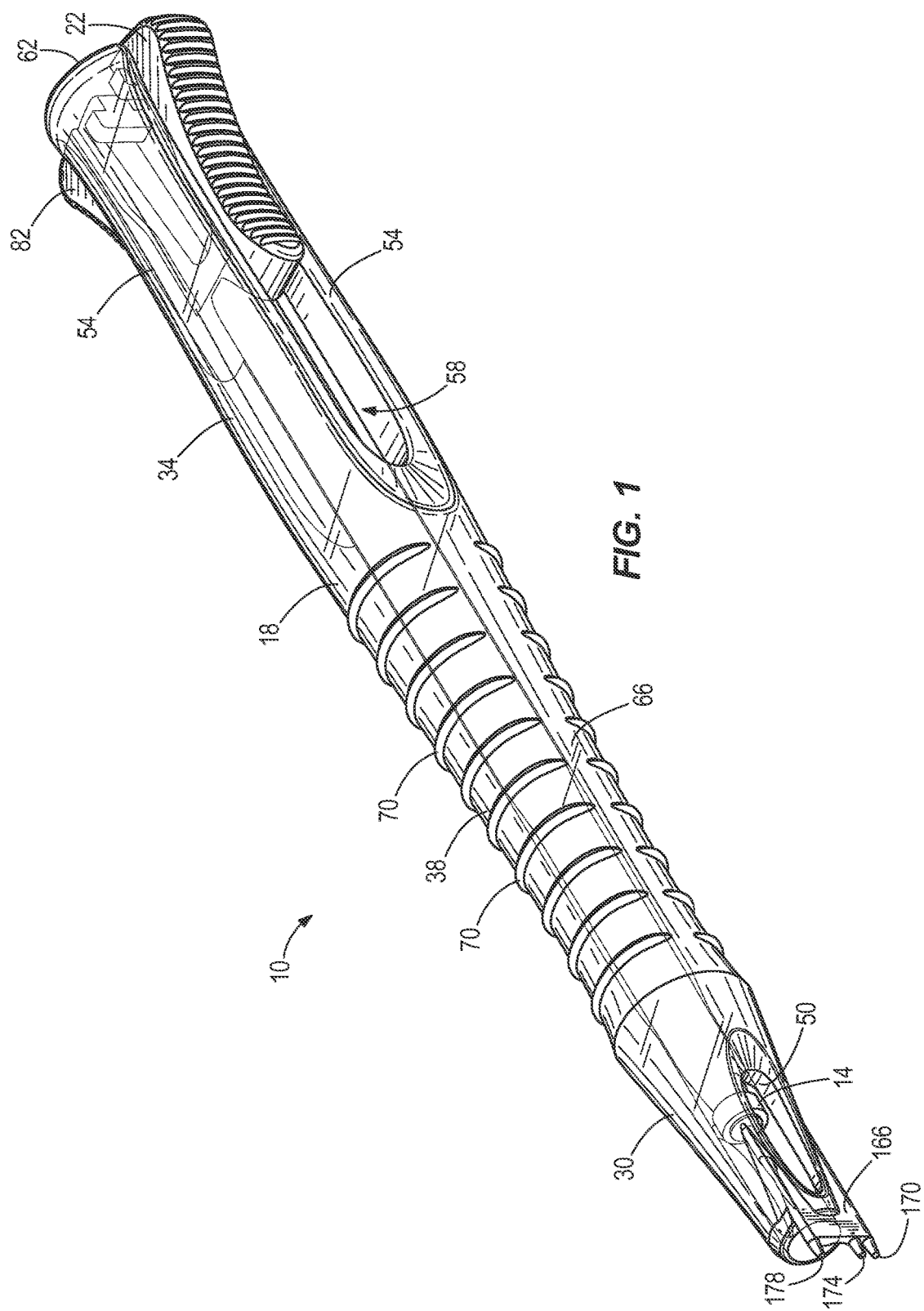
FIG. 1 is a perspective view of a cannula insertion tool including a slider and a needle in a first position.
Figure 2:
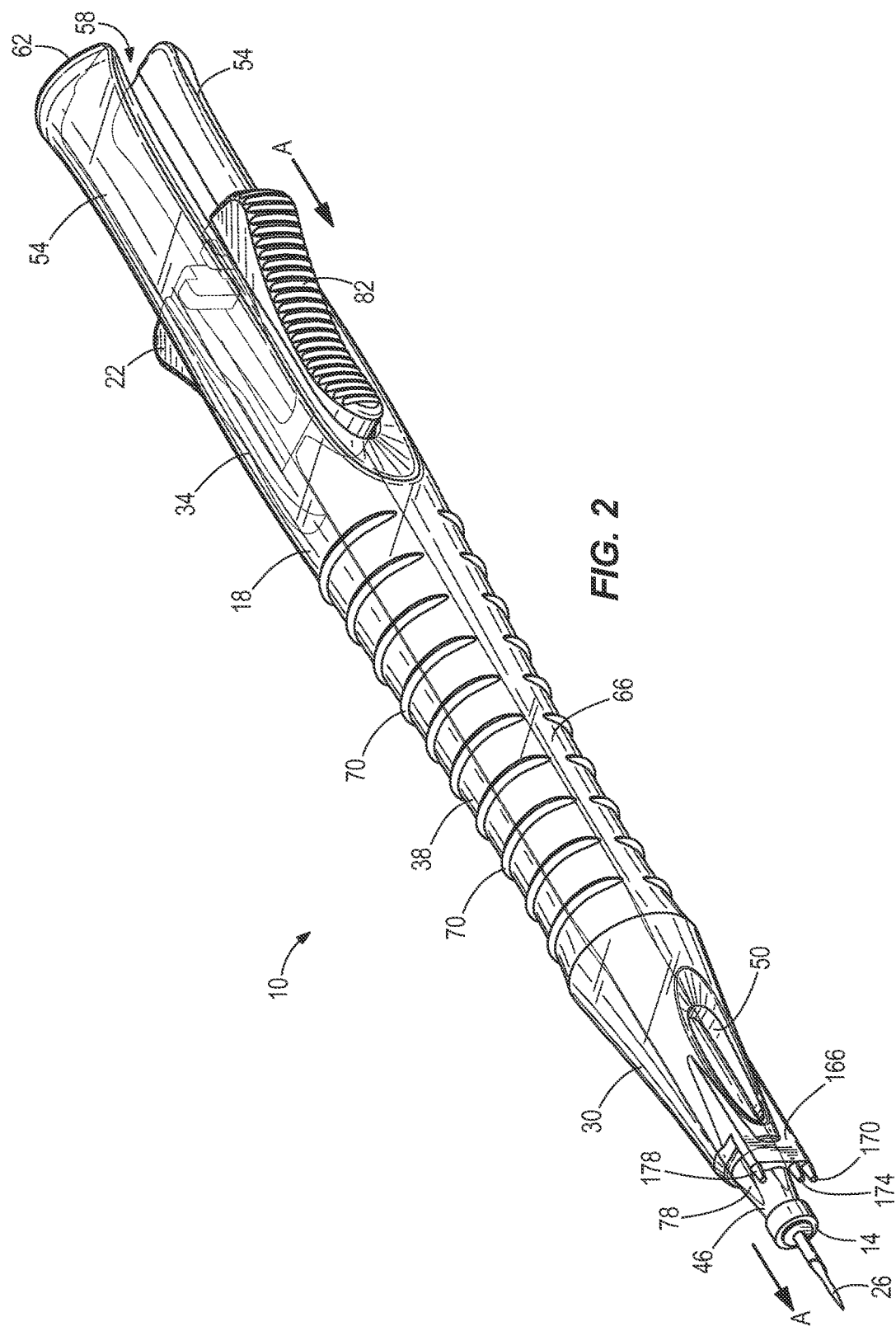
FIG. 2 is a perspective view of the cannula insertion tool with the slider and the needle in a second position.
Figure 3:
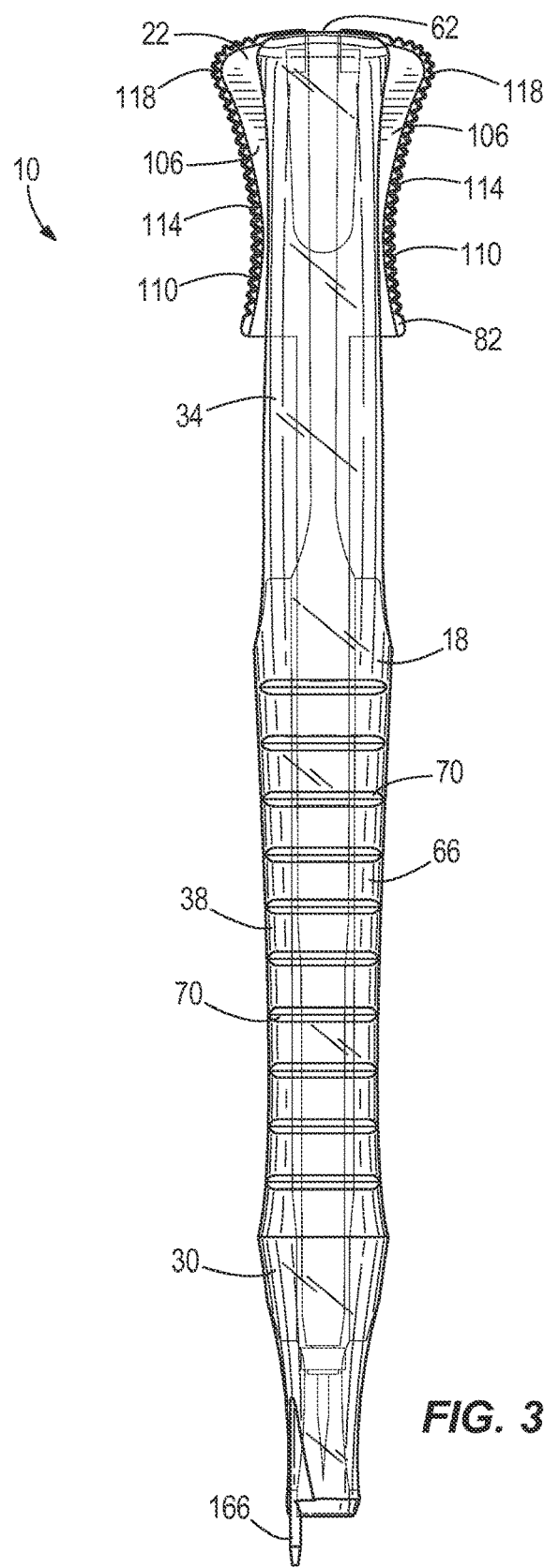
FIG. 3 is a side view of the cannula insertion tool with the slider and the needle in the first position.

FIGS. 1-3 illustrate a cannula insertion tool 10. The insertion tool 10 is operable to insert a cannula 14, or other hollow tube or member, into a patient. In the illustrated embodiment, the insertion tool 10 is configured for one-handed operation by a user to insert the cannula 14 into an eye of the patient. In other embodiments, the insertion tool 10 may be configured to insert the cannula 14 into other portions of a patient's body, such as a vein or trachea.

The illustrated cannula insertion tool 10 includes a body 18, a slider 22, and a needle 26. The body 18 has an overall cylindrical shape to facilitate being held in one hand by a user. The body 18 includes a first end portion 30, a second end portion 34 opposite the first end portion 30, and a grip 38 located between the first and second end portions 30 and 34. The body 18 also includes a longitudinal axis 42 (FIG. 4) extending through the end portions 30 and 34 and the grip 38. In the illustrated embodiment, the end portions 30 and 34 and the grip 38 are integrally formed (e.g., molded) as a single piece. In other embodiments, the end portions 30 and 34 and the grip 38 may be separate pieces that are permanently or removably coupled together. In some embodiments, such as the illustrated embodiment, the body 18 is made of a transparent or semi-transparent material (e.g., clear or translucent plastic), but may alternatively be made of an opaque material.

The first end portion 30 of the body 18 extends from one end of the grip 38 generally along the longitudinal axis 42. In the illustrated embodiment, the first end portion 30 tapers (i.e., decreases in diameter) as it extends away from the grip 38. As shown in FIG. 1, the first end portion 30 is shaped and sized to receive and house the needle 26 and a distal portion 46 (FIG. 2) of the slider 22. The illustrated first end portion 30 also defines two openings 50, or viewing windows, on opposite sides of the body 18. The openings 50 facilitate viewing and accessing the cannula 14 and the needle 26 through sides of the body 18.

The second end portion 34 of the body 18 extends from an end of the grip 38 opposite the first end portion 30 and generally along the longitudinal axis 42. The illustrated second end portion 34 includes two spaced apart arms 54 that define a slot 58. The slot 58 extends through opposing sides and an end 62 of the body 18. The slot 58 is configured to receive a portion of the slider 22 between the arms 54. The arms 54 help support and guide the slider 22 during movement of the slider 22 relative to the body 18. By extending through the body 18 to form an opening in the end 62 of the body 18, the slot 58 also facilitates assembling the slider 22 with the body 18. In particular, the slot 58 allows the slider 22 to be inserted into the body 18 through the end 62 of the second end portion 34.

The grip 38 is located between the first end portion 30 and the second end portion 34 to facilitate holding the body 18. The illustrated grip 38 is generally cylindrical and includes a contoured outer surface 66. The outer surface 66 is concave toward the longitudinal axis 42 of the body 18 such that a midsection of the grip 38 is smaller in diameter than the ends of the grip 38 adjacent the first and second end portions 30, 34. The grip 38 also includes spaced apart ribs 70 formed on the outer surface 66. The ribs 70 are arranged in parallel and extend outwardly from the outer surface 66 to facilitate grasping and holding the body 18 at the grip 38.

Figure 4:
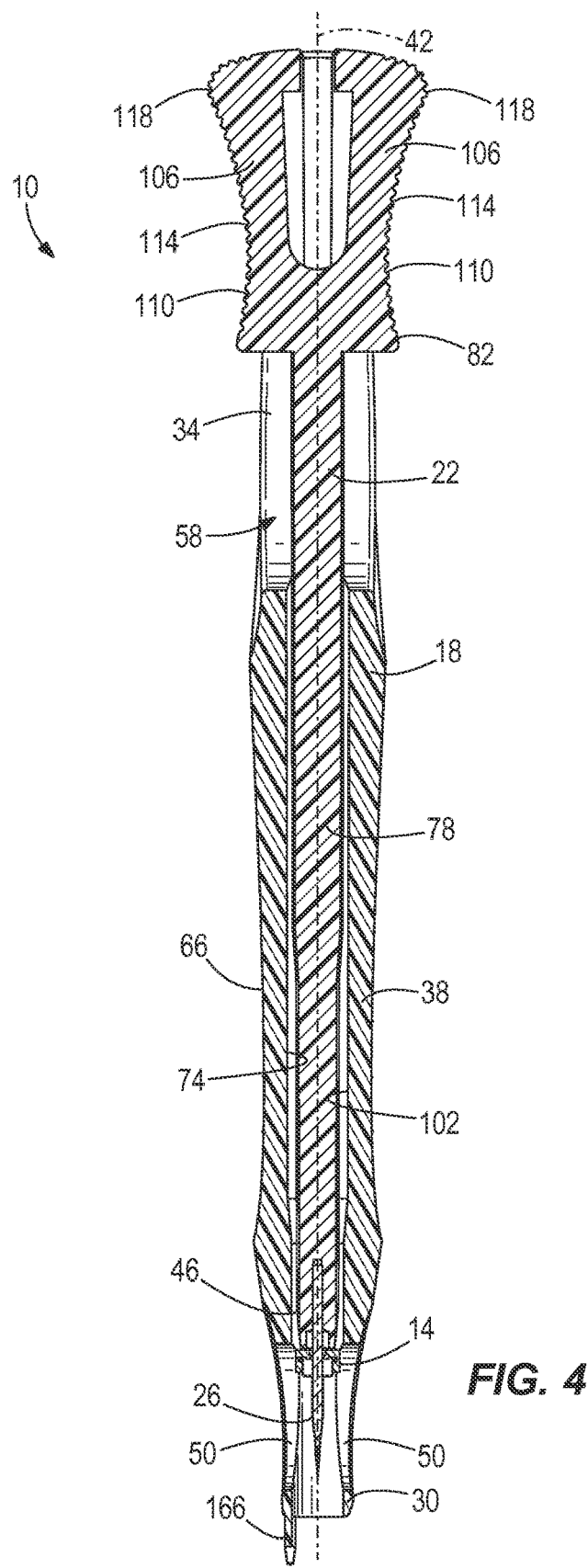
FIG. 4 is a cross-sectional view of the cannula insertion tool with the slider and the needle in the first position.

As shown in FIG. 4, the body 18 also defines a channel 74 that receives at least a portion of the slider 22. The channel 74 extends through the first end portion 30 and the grip 38. The channel 74 also communicates with the slot 58 in the second end portion 34 to receive the slider 22 as the slider 22 is inserted into the body 18 through the second end portion 34. The illustrated channel 74 is generally coaxial with the longitudinal axis 42 of the body 18. In other embodiments, the channel 74 may be offset from the longitudinal axis 42 of the body 18.

Figure 5:
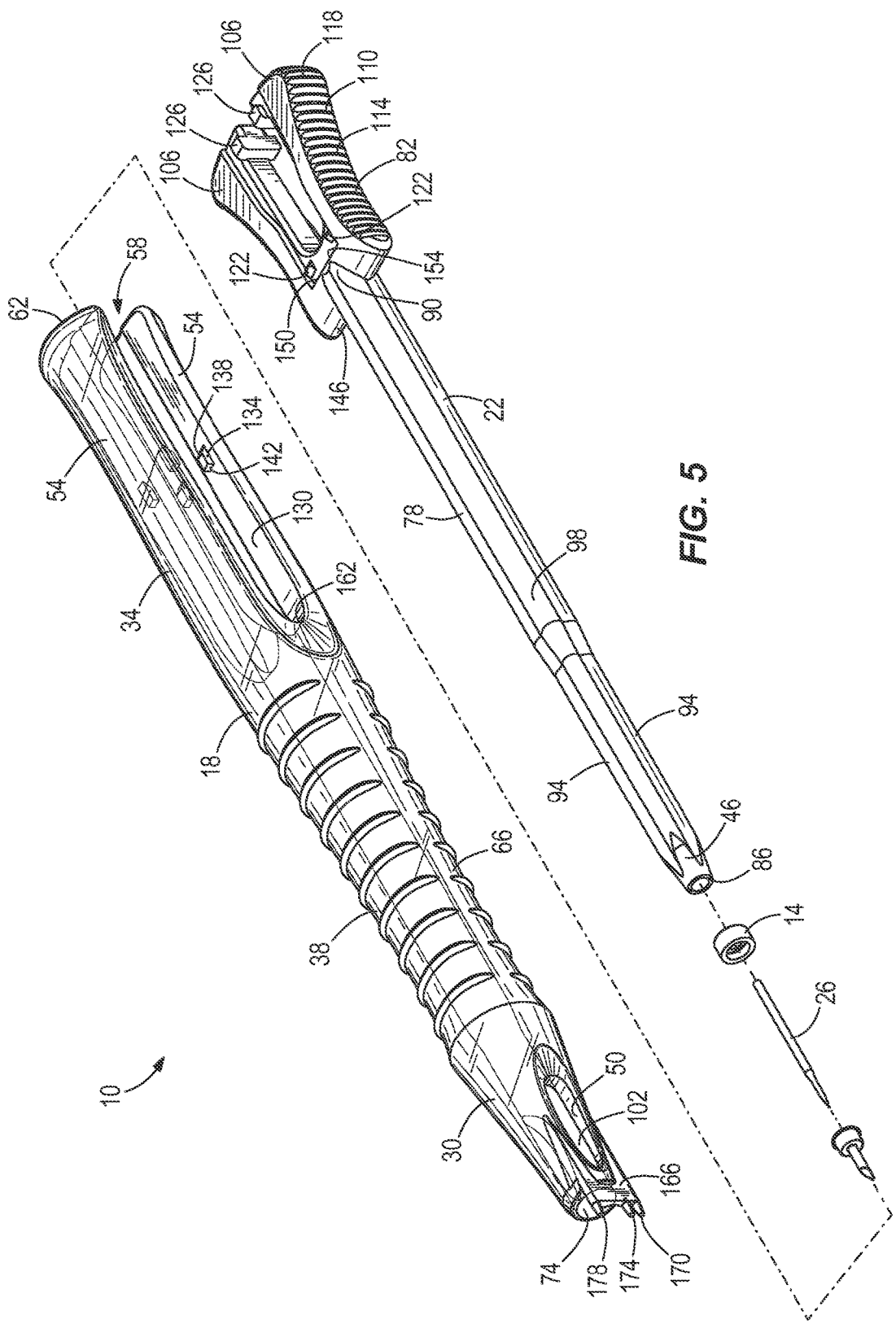
FIG. 5 is an exploded perspective view of the cannula insertion tool.

As shown in FIG. 5, the slider 22 includes a drive member 78 and an actuator 82. In the illustrated embodiment, the drive member 78 and the actuator 82 are integrally formed as a single piece. In other embodiments, the drive member 78 and the actuator 82 may be separate pieces that are permanently or removably coupled together. When the slider 22 is assembled with the body 18, the drive member 78 is positioned within the channel 74 of the body 18, and the actuator 82 is positioned partially within the slot 58 in the second end portion 34 of the body 18. The slider 22 is movable relative to the body 18 between a first, or retracted, position (FIGS. 1 and 3) and a second, or extended, position (FIG. 2). In the illustrated embodiment, the slider 22 slides within the channel 74 of the body 18 generally along the longitudinal axis 42 (FIG. 4) between the retracted and extended positions.

The illustrated drive member 78 is an elongated shaft having a first end 86 and a second end 90. The needle 26 is coupled to the first end 86 of the drive member 78. The actuator 82 is coupled to the second end 90 of the drive member 78. The drive member 78 includes an outer surface having longitudinally-extending grooves 94 and protrusions 98. The protrusions 98 contact an inner surface 102 of the body 18 that defines the channel 74 to support the drive member 78 within the channel 74. The illustrated protrusions 98 provide a relatively small surface area over which the drive member 78 contacts the inner surface 102 of the body 18 (compared to a cylindrical drive shaft with a continuous outer surface) to facilitate sliding the slider 22 within the channel 74. The grooves 94 and the protrusions 98 also create spaces or gaps between the slider 22 and the body 18 to facilitate cleaning the insertion tool 10. In particular, the grooves 94 and the protrusions 98 allow the tool 10 to be washed while assembled since water (or other fluid) can easily flow into, drain out of, and evaporate out of the tool 10 without any need to disassemble the slider 22 from the body 18.

The actuator 82 is configured to be engaged by a user during operation of the insertion tool 10 to move the slider 22 relative to the body 18. The illustrated actuator 82 is generally U-shaped and includes two legs 106. The legs 106 are connected together at the second end 90 of the drive member 78 and extend generally parallel to each other. A portion of each leg 106 extends outwardly from between the arms 54 of the second end portion 34. In particular, each leg 106 extends beyond an outer periphery of the body 18 (i.e., the outermost boundary defined by an outer surface of the body 18) so that the actuator 82 is easier to access and engage for a user.

As shown in FIG. 3, the illustrated actuator 82 includes two engagement surfaces 110 positioned on opposite sides of the body 18. The engagement surfaces 110 are formed on the legs 106 such that the surfaces 110 are located outside of the outer periphery of the body 18. Each engagement surface 110 is contoured to facilitate engagement by the user. In particular, a first section 114 of each engagement surface 110 that is relatively close to the drive member 78 is concave toward the body 18. A second section 118 of each engagement surface 110 that is relatively far from the drive member 78 is convex away from the body 18 to form a bump or protrusion. In the illustrated embodiment, the engagement surfaces 110 of the actuator 82 are also ribbed. The ribbed surfaces 110 facilitate engaging the actuator 82 with a thumb during one-handed operation of the insertion tool 10.

As shown in FIG. 5, the illustrated slider 22 also includes ribs 122, 126 formed on the actuator 82. A first set of ribs 122, or projections, is formed on the actuator 82 adjacent the drive member 78. A second set of ribs 126, or projections, is formed adjacent an end of the actuator 82 opposite from the drive member 78. The ribs 122, 126 extend outwardly from the actuator 82 toward an inner surface 130 of the second end portion 34 of the body 18. The ribs 122, 126 are configured to engage corresponding ribs 134, or projections, formed on the second end portion 34 of the body 18.

The ribs 134 of the body 18 extend from the inner surface 130 of the second end portion 34 toward the actuator 82. Each of the ribs 134 on the body 18 includes a ramped surface 138 and a shoulder surface 142. The ramped surfaces 138 are angled relative to the inner surface 130 to allow movement of the slider 22 relative to the body 18 in direction A (FIG. 2) if sufficient force is applied to the slider 22. The shoulder surfaces 142 extend generally perpendicularly from the inner surface 130 to inhibit movement of the slider 22 relative to the body 18 in a direction opposite the direction A, regardless of the force applied to the slider 22.

When assembling the slider 22 with the body 18, the slider 22 is inserted into the body 18 with sufficient force to slide a rounded end 146 of the actuator 82 that is adjacent the drive member 78 past the ribs 134 on the body 18. As the slider 22 is being inserted into the body 18, the rounded end 146 of the actuator 82 engages the ramped surfaces 138 of the ribs 134 on the body 18. The ribs 134 on the body 18 ride up the actuator 82 to slide over the rounded end 146 and into recesses 150 formed between the first ribs 122 on the actuator 82 and lips 154 of the actuator 82. The spaced apart configuration of the arms 54 of the second end portion 34 allows the arms 54 to temporarily deflect away from each other to provide clearance for the actuator 82 until the ribs 134 on the body 18 align with and snap into the recesses 150 in the actuator 82.

Figure 6:
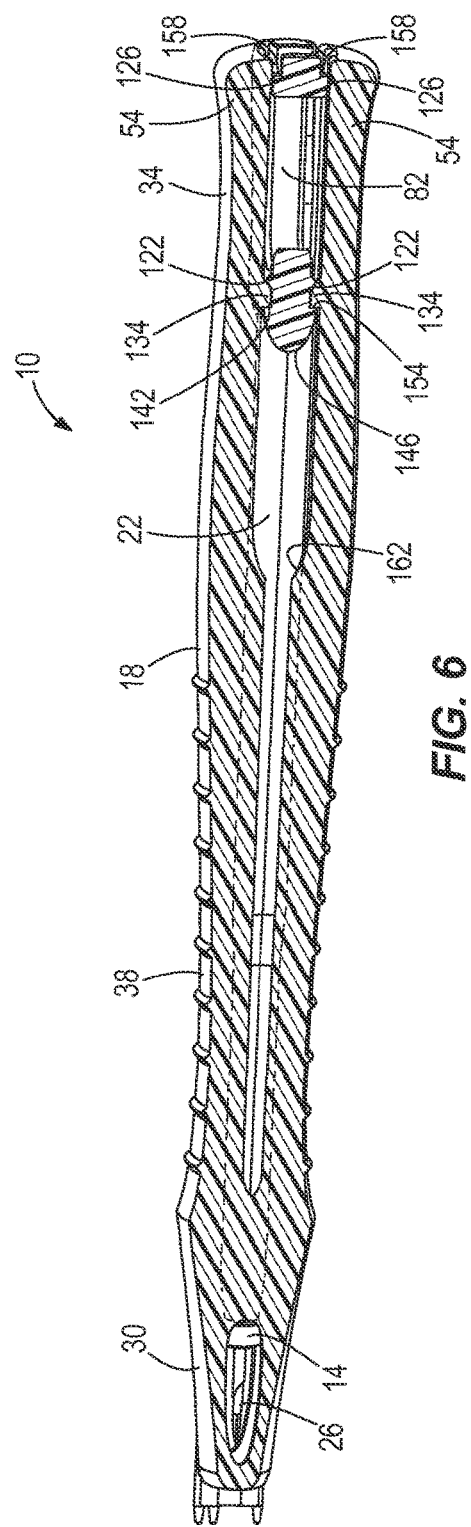
FIG. 6 is another cross-sectional view of the cannula insertion tool with the slider and the needle in the first position.

As shown in FIG. 6, the ribs 134 on the body 18 extend into the recesses 150 formed between the first ribs 122 and the lips 154 of the actuator 82 when the slider 22 is in the retracted position. The lips 154 of the actuator 82 engage the shoulder surfaces 142 of the ribs 134 on the body 18 to inhibit the slider 22 from being pulled out of the body 18. As such, the slider 22 is inhibited from sliding out of the body 18 after the slider 22 is installed in the body 18. In addition, the recesses 150 in the actuator 82 are shaped and sized to generally match the shape and size of the ribs 134 on the body 18. The ribs 134 fit snugly within the recesses 150 when the slider 22 is in the refracted position so that the slider 22 does not rattle or shift within the body 18.

To move the slider 22 to the extended position (FIG. 2), the slider 22 is pushed with sufficient force in the direction A so the ribs 134 on the body 18 slide out of the recesses 150 and over the first ribs 122 on the actuator 82. Continued movement of the slider 22 relative to the body 18 in the direction A brings the ribs 134 on the body 18 into engagement with the second ribs 126 on the actuator 82. The ribs 134 on the body 18 also slide over and past the second ribs 126 on the actuator 82 to clear the second ribs 126. Sliding the second ribs 126 past the ribs 134 provides a tactile and/or audible indicator to the user that the slider is properly positioned in the extended position.

Figure 7:
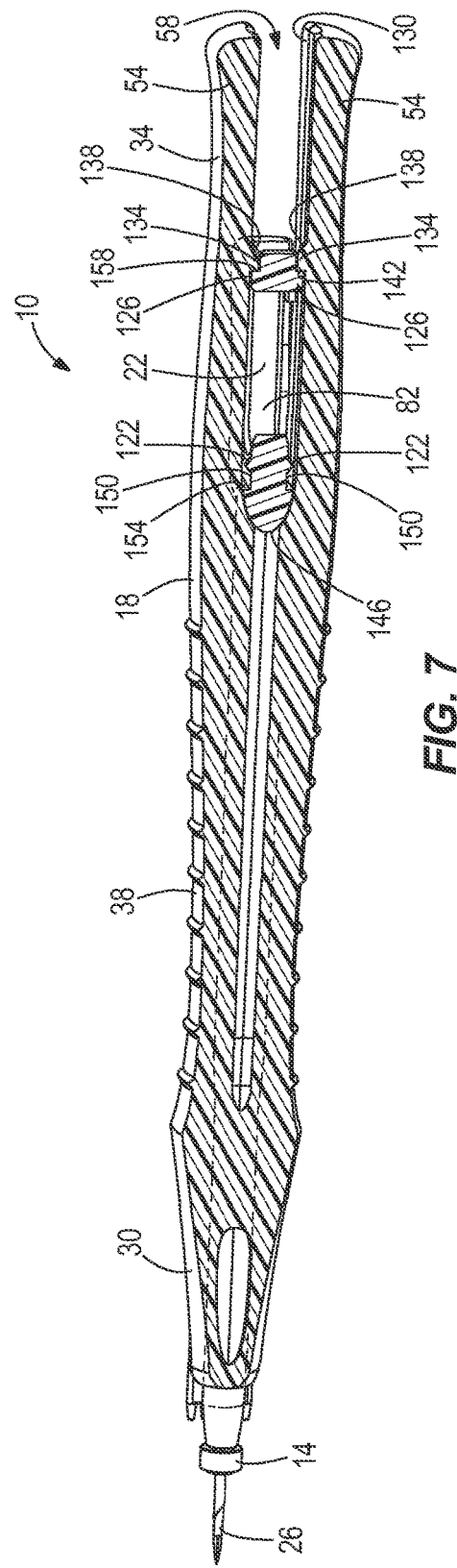
FIG. 7 is the cross-sectional view of the cannula insertion tool shown in FIG. 6 with the slider and the needle in the second position.

As shown in FIG. 7, when the slider 22 is in the extended position, shoulder surfaces 158 of the second ribs 126 on the actuator 82 engage the shoulder surfaces 142 of the ribs 134 on the body 18 to inhibit the second ribs 126 from sliding over and past the ribs 134 on the body 18 in the direction opposite the direction A. As such, the slider 22 is inhibited from sliding from the extended position (FIG. 2) back to the retracted position (FIGS. 1 and 3). Furthermore, the legs 106 of the actuator 82 are shaped and sized to be captured between the ribs 134 on the body 18 and a curved bottom surface 162 (FIG. 5) of the second end portion 34 that defines the slot 58. Such an arrangement inhibits the slider 22 from shifting within the body 18 when the slider 22 is in the extended position.

If necessary, the slider 22 can be moved from the extended position (FIG. 2) back to the refracted position (FIGS. 1 and 3) by squeezing the legs 106 of the actuator 82 together. Squeezing the actuator 82 moves the legs 106 toward each other so that the second ribs 126 on the actuator 82 are moved out of alignment with the ribs 134 on the body 18. The slider 22 can then be pulled past the ribs 134 on the body 18 in the direction opposite the direction A without the ribs 126, 134 contacting each other.

As shown in FIG. 4, the needle 26, or blade, is coupled to the first end 90 of the drive member 78 opposite from the actuator 82. The needle 26 extends from the drive member 78 and supports the cannula 14. The needle 26 is fixed to the drive member 78 of the slider 22 for movement with the slider 22 relative to the body 18. The needle 26 is configured to puncture body tissue (e.g., an eye, a vein, a trachea, etc.) to insert the cannula 14 into a patient.

During use, the needle 26 is movable with the slider 22 relative to the body 18 between the retracted position (FIGS. 1 and 3) and the extended position (FIG. 2). When in the retracted position, as shown in FIGS. 1 and 3, the needle or blade 26 is positioned substantially within the first end portion 30 of the body 18. In this position, no portion of the needle 26 extends beyond the outer periphery of the body 18. Such an arrangement reduces the possibility of a user unintentionally contacting the needle 26 and accidentally cutting himself. Thus, the ability of the needle to be retracted increases user safety. Another benefit of retractability and storage of the needle within the body 18 is that the needle is protected from physical damage when positioned within the body 18. When in the extended position, as shown in FIG. 2, the needle 26 extends outwardly from the first end portion 30 of the body 18 for use. In this position, the needle 26 can be inserted into body tissue (e.g., an eye, etc.) of a patient to install the cannula 14 in the body tissue.

Referring to FIGS. 1 and 2, the cannula insertion tool 10 also includes a scleral marker 166 coupled to the body 18. In the illustrated embodiment, the scleral marker 166 is integrally formed (e.g., molded) with and extends from the first end portion 30 of the body 18 in a direction generally parallel to the longitudinal axis 42 (FIG. 4) of the body 18. In other embodiments, the scleral marker 166 may be a separate element that is removably or permanently coupled to the body 18. The illustrated scleral marker 166 includes three projections 170, 174, 178 extending outwardly from the body 18. Two of the projections 170, 174 are positioned relatively close together adjacent one edge of the marker 166. The third projection 178 is spaced relatively far from the other two projections 170, 174 adjacent an opposite edge of the marker 166.

The projections 170, 174, 178 are configured to temporarily mark body tissue (e.g., portions of an eye, etc.) of a patient to create a target on the body tissue for the needle 26. When the needle 26 is in the retracted position (FIGS. 1 and 3), the scleral marker 166 is the only element of the cannula insertion tool 10 that extends from the first end portion 30 of the body 18. The scleral marker 166 can, therefore, be pushed against the body tissue to mark the body tissue without interference from the needle 26. In the illustrated embodiment, the scleral marker 166 extends a relatively short distance from first end portion 30 of the body 18. As such, when the needle 26 is in the extended position (FIG. 2), the distal portion 46 of the drive member 78 also extends out of the first end portion 30 so that the needle 26 and the cannula 14 are both located further from the first end portion 30 of the body 18 than the projections 170, 174, 178 of the scleral marker 166. Such an arrangement allows the needle 26 and the cannula 14 to be used and inserted into a patient without interference from the marker 166.

Figure 8:
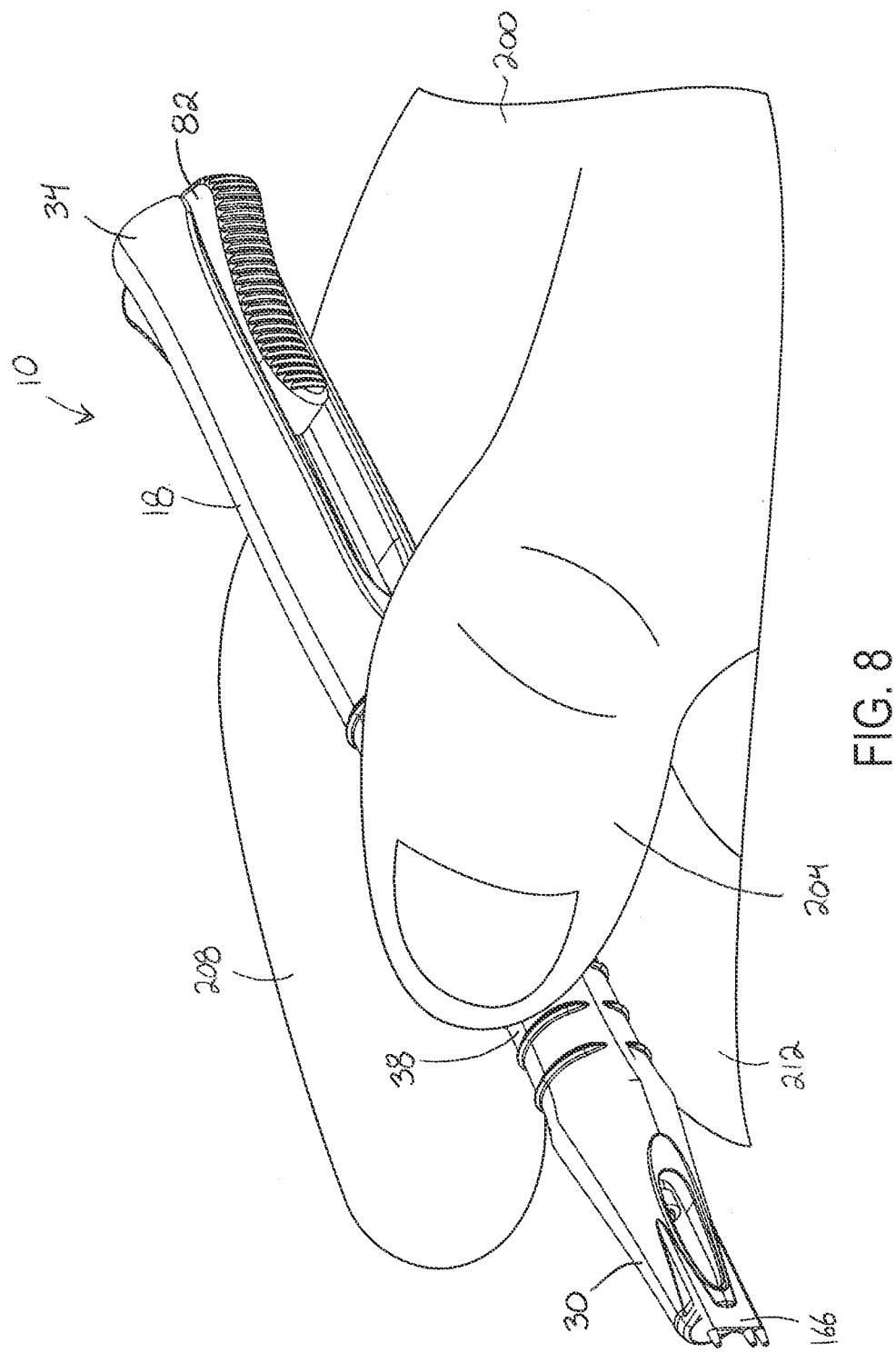
FIG. 8 illustrates a user holding the cannula insertion tool in a single hand.

As shown in FIG. 8, the illustrated cannula insertion tool 10 is configured to be operated by a user entirely with one hand 200. The grip 38 of the body 18 is located between the end portions 30, 34 so that the user can grasp and hold the tool 10 with his or her fingers (like holding a pen or pencil). In particular, the user holds the tool 10 between his or her thumb 204, pointer or index finger 208, and middle finger 212.

The actuator 82 of the slider 22 extends from the second end portion 34 of body 18 opposite from the needle 26 so that the actuator 82 can be engaged and actuated by the thumb 204 of the user while the user is supporting the grip 38 with his or her other fingers 208, 212. The user simply moves his or her thumb 204 into engagement with the actuator 82 and pushes the actuator 82 forward (i.e., toward the first end portion 30) to move the needle 26 to the extended position (FIG. 2). The legs 106 of the actuator 82 extend from opposite sides of the body 18 to minimize the amount the body 18 might need to be rotated to properly align one of the engagement surfaces 110 of the actuator 82 with the user's thumb 204.

Positioning the scleral marker 166 on the same end portion 30 of the body 18 as where the needle 26 is located allows the user to use both the marker 166 and the needle 26 without having to spin or flip the cannula insertion tool 10 in his or her hand 200. As such, the user does not have to take his or her eyes off of, for example, a microscope after using the scleral marker 166 and use two hands to extend the needle 26. Stated another way, the configuration of the tool 10 permits one-handed operation to extend and retract the needle 26 and permits the scleral marker 166 to be positioned on the front end of the tool 10. Thus, a user may mark the surgical site (with the needle 26 retracted), extend the needle 26, and make an incision using one hand while maintaining his or her visual focus on the surgical microscope.

Various features and advantages of the invention are set forth in the following claims.

What is claimed is:

1. A cannula insertion tool comprising:
    a body including a first end portion, a second end portion, and a grip located between the first end portion and the second end portion, the body defining a channel extending through the first end portion and the grip, the body having a longitudinal axis extending through the first end portion, the grip, and the second end portion, wherein the grip is generally cylindrical and an outer surface of the grip is concave toward the longitudinal axis;
    a slider including a drive member and an actuator, the drive member positioned within the channel of the body, the actuator extending outwardly from the second end portion of the body;
    a needle coupled to the drive member adjacent the first end portion of the body, the needle movable with the slider between a retracted position, in which the needle is positioned substantially within the first end portion of the body, and an extended position, in which at least a portion of the needle extends outwardly from the first end portion of the body; and
    a cannula supported by the needle, the cannula being movable with the needle between the retracted position and the extended position,
    wherein the grip is located between the needle and the actuator of the slider when the needle is in both the retracted position and the extended position.

2. The cannula insertion tool of claim 1, wherein the drive member has a first end and a second end, wherein the needle is coupled to the first end of the drive member, and wherein the actuator is coupled to the second end of the drive member.

3. The cannula insertion tool of claim 2, wherein the drive member and the actuator of the slider are integrally formed as a single piece.

4. The cannula insertion tool of claim 1, wherein the needle and the slider are movable between the retracted and extended positions generally along the longitudinal axis.

5. The cannula insertion tool of claim 1, wherein the grip includes a plurality of spaced apart ribs to facilitate grasping the body.

6. The cannula insertion tool of claim 1, wherein the actuator includes an engagement surface, and wherein the actuator extends beyond an outer periphery of the body such that the engagement surface is located outside of the outer periphery of the body.

7. The cannula insertion tool of claim 6, wherein at least a portion of the engagement surface is concave toward the body.

8. The cannula insertion tool of claim 6, wherein the engagement surface is a first engagement surface, and wherein the actuator includes a second engagement surface located outside of the outer periphery of the body on an opposite side of the second end portion than the first engagement surface.

9. The cannula insertion tool of claim 1, wherein the second end portion includes two spaced apart arms, and wherein the actuator is positioned between the two spaced apart arms.

10. The cannula insertion tool of claim 1, wherein the second end portion of the body includes a first rib, wherein the actuator includes a second rib, and wherein the second rib engages the first rib when the slider is in the extended position to inhibit movement of the slider relative to the body.

11. The cannula insertion tool of claim 10, wherein the actuator defines a recess spaced apart from the second rib, and wherein the first rib of the body fits within the recess in the actuator when the slider is in the retracted position to inhibit movement of the slider relative to the body.

12. The cannula insertion tool of claim 1, wherein the drive member includes a plurality of longitudinally-extending protrusions that contacts an inner surface of the body to support the drive member within the channel.

13. The cannula insertion tool of claim 1, further comprising a scleral marker coupled to the body.

14. The cannula insertion tool of claim 13, wherein the scleral marker extends from the first end portion of the body.

15. A cannula insertion tool comprising:
    a body including an end portion and a grip, the body defining a channel extending through the end portion and the grip, the body having a longitudinal axis extending through the end portion and the grip, wherein the grip is generally cylindrical and an outer surface of the grip is concave toward the longitudinal axis;
    a slider including a drive member and an actuator, the drive member positioned within the channel of the body, the actuator extending outwardly from the body;

a needle coupled to the drive member adjacent the end portion of the body, the needle movable with the slider between a retracted position, in which the needle is positioned substantially within the body, and an extended position, in which at least a portion of the needle extends outwardly from the end portion of the body;

a scleral marker coupled to and extending from the end portion of the body; and a cannula supported by the needle, the cannula being movable with the needle between the retracted position and the extended position, wherein the grip is located between the needle and the actuator of the slider when the needle is in both the retracted position and the extended position.

16. The cannula insertion tool of claim 15, wherein the scleral marker includes a plurality of projections.

17. The cannula insertion tool of claim 16, wherein the scleral marker includes three projections, wherein two of the three projections are positioned relatively close to each other, and wherein the other projection is spaced relatively far from the two of the three projections.

18. The cannula insertion tool of claim 15, wherein the needle and the slider are movable between the retracted and extended positions generally along the longitudinal axis.

19. The cannula insertion tool of claim 18, wherein the scleral marker extends from the body in a direction generally parallel to the longitudinal axis.

20. A cannula insertion tool comprising:
a body including a first end portion, a second end portion, a grip located between the first end portion and the second end portion, and a longitudinal axis extending through the first end portion, the grip, and the second end portion, the body defining a channel extending through the first end portion and the grip, wherein the grip is generally cylindrical and an outer surface of the grip is concave toward the longitudinal axis;

a slider including a drive member and an actuator, the drive member positioned within the channel of the body and having a first end and a second end, the actuator coupled to the second end of the drive member and extending outwardly from the second end portion of the body;

a needle coupled to the first end of the drive member adjacent the first end portion of the body, the needle movable with the slider along the longitudinal axis between a retracted position, in which the needle is positioned substantially within the first end portion of the body, and an extended position, in which at least a portion of the needle extends outwardly from the first end portion of the body;

a scleral marker coupled to and extending from the first end portion of the body in a direction generally parallel to the longitudinal axis; and a cannula supported by the needle, the cannula being movable with the needle between the retracted position and the extended position, wherein the grip is located between the needle and the actuator of the slider when the needle is in both the retracted position and the extended position.

21. A method of performing an ophthalmic surgical procedure, the method comprising:
grasping an insertion tool with a single human hand, the insertion tool including
a body having an end portion, a grip, and a channel extending through the end portion and the grip, the body having a longitudinal axis extending through the end portion and the grip, wherein the grip is generally cylindrical and an outer surface of the grip is concave toward the longitudinal axis,
a slider having a drive member and an actuator, the drive member positioned within the channel of the body, the actuator extending outwardly from the body,
a needle coupled to the drive member adjacent the end portion of the body, the needle movable with the slider between a retracted position, in which the needle is positioned substantially within the body, and an extended position, in which at least a portion of the needle extends outwardly from the end portion of the body,
a scleral marker coupled to and extending from the end portion of the body, and
a cannula supported by the needle, the cannula being movable with the needle between the retracted position and the extended position,
wherein the grip is located between the needle and the actuator of the slider when the needle is in both the retracted position and the extended position;
marking a surgical site with the scleral marker while the insertion tool is grasped in the single human hand; and
moving the needle and the cannula to the extended position while the insertion tool is grasped in the single human hand.

22. The method of claim 21, wherein the actuator extends from another end of the body opposite the scleral marker; and
wherein moving the needle to the extended position includes sliding the actuator toward the one end of the body with the single human hand while the insertion tool is grasped in the single human hand.

23. The method of claim 22, wherein grasping the insertion tool includes grasping the grip of the body with the single human hand.

24. The method of claim 21, wherein the scleral marker extends axially further from the body than the needle when the needle is in the retracted position, and wherein moving the needle to the extended position includes moving the needle so that the needle extends axially further from the body than the scleral marker.

* * * * *